US012746406B2

(12) United States Patent
Halavee et al.

(10) Patent No.: US 12,746,406 B2
(45) Date of Patent: Sep. 29, 2026

(54) GEOMETRICALLY FITTED TRANSDUCERS FOR TUMOR TREATING FIELDS

(71) Applicant: Novocure GmbH, Root (CH)

(72) Inventors: Noa Halavee, Tel Aviv (IL); Shalom Strauss, Haifa (IL)

(73) Assignee: Novocure GmbH, Baar (CH)

( * ) Notice: Subject to any disclaimer, the term of this patent is extended or adjusted under 35 U.S.C. 154(b) by 389 days.

(21) Appl. No.: 18/124,307

(22) Filed: Mar. 21, 2023

(65) Prior Publication Data

US 2023/0302289 A1 Sep. 28, 2023

Related U.S. Application Data

(60) Provisional application No. 63/322,530, filed on Mar. 22, 2022.

(51) Int. Cl.
*A61N 1/40* (2006.01)
*A61N 1/04* (2006.01)

(52) U.S. Cl.
CPC ............. *A61N 1/40* (2013.01); *A61N 1/0492* (2013.01)

(58) Field of Classification Search
None
See application file for complete search history.

(56) References Cited

U.S. PATENT DOCUMENTS 4,462,412 A 7/1984 Turner
7,565,205 B2 7/2009 Palti
2020/0114142 A1* 4/2020 Bomzon ................ G16H 50/50
2020/0171297 A1* 6/2020 Kirson ................. A61N 1/0496
2021/0162228 A1 6/2021 Urman et al.
2021/0220640 A1 7/2021 Deslauriers
2022/0305275 A1* 9/2022 Schwarz .................. A61N 7/00
2024/0325743 A1* 10/2024 Rynerson ........... A61N 1/36153
2025/0177743 A1* 6/2025 Chen .................. A61N 1/36002

FOREIGN PATENT DOCUMENTS

CN 113164745 7/2021
WO WO-2008/135956 A2 11/2008
WO WO-2020/110050 A1 6/2020

OTHER PUBLICATIONS

International Search Report cited in PCT/IB2023/052828 dated Jun. 20, 2023.

* cited by examiner

*Primary Examiner* — Michael W Kahelin
(74) *Attorney, Agent, or Firm* — McCarter & English, LLP; Michael A. Sartori

(57) ABSTRACT

A transducer apparatus for delivering tumor treating fields to a subject's body, the transducer apparatus including: an array of electrode elements, the array configured to be positioned over the subject's body with a face of the array facing the subject's body; wherein, when viewed from a direction perpendicular to the face of the array, an outer perimeter of the array substantially tracing the electrode elements has a shape including: at least one convex edge portion protruding away from a centroid of the array; and at least one concave edge portion recessed toward the centroid of the array.

19 Claims, 5 Drawing Sheets

GEOMETRICALLY FITTED TRANSDUCERS FOR TUMOR TREATING FIELDS

CROSS REFERENCE TO RELATED APPLICATIONS

This application claims priority to U.S. Provisional Patent Application No. 63/322,530, filed Mar. 22, 2022, which is hereby incorporated by reference in its entirety.

BACKGROUND

Tumor treating fields (TTFields) are low intensity alternating electric fields within the intermediate frequency range, which may be used to treat tumors as described in U.S. Pat. No. 7,565,205. TTFields are induced non-invasively into the region of interest by transducers placed on the patient's body and applying AC voltages between the transducers. Conventionally, transducers used to generate TTFields include a plurality of ceramic disks. One side of each ceramic disk is positioned against the patient's skin, and the other side of each disc has a conductive backing. Electrical signals are applied to this conductive backing, and these signals are capacitively coupled into the patient's body through the ceramic discs. Conventional transducer designs include rectangular arrays of ceramic disks aligned with each other in straight rows and columns and attached to the subject's body via adhesive.

SUMMARY OF THE INVENTION

One aspect of the invention is directed to a transducer apparatus for delivering tumor treating fields to a subject's body, the transducer apparatus including: an array of electrode elements, the array configured to be positioned over the subject's body with a face of the array facing the subject's body; wherein, when viewed from a direction perpendicular to the face of the array, an outer perimeter of the array substantially tracing the electrode elements has a shape including: at least one convex edge portion protruding away from a centroid of the array; and at least one concave edge portion recessed toward the centroid of the array.

The above aspect of the invention is exemplary, and other aspects and variations of the invention will be apparent from the following detailed description of embodiments.

DESCRIPTION OF EMBODIMENTS

This application describes exemplary transducer apparatuses and assemblies used to apply TTFields to a subject's body for treating one or more cancers. This application also describes exemplary methods to apply TTFields to a subject's body using transducers.

Transducers used to apply TTFields to a subject's body often include multiple electrode elements coupled together on a substrate and attached to the subject's body at a desired location, for example, via an adhesive layer on the substrate or a separately applied adhesive. Conventional transducers have large, rectangular surfaces so as to maximize a number of electrode elements that are located on the transducer for applying TTFields to the subject's body. However, the rectangular design can be too large for placement on smaller subject's bodies or on smaller regions (e.g., a head) of subject's bodies without overlapping other transducers.

The inventors have now recognized that a need exists for transducers that are geometrically shaped to enable placement of larger transducers with a greater number of electrode elements on a subject's body without the transducers overlapping each other. In particular, transducers that are shaped to geometrically fit amongst other transducers in an assembly of transducers may enable the placement of more electrode elements on smaller portions of a subject's body, such as on the subject's head. As a result, the transducers can induce TTFields at an ideal location and with a greater power level for targeting a region of interest (e.g., tumor) in the subject's body, thereby improving patient outcomes.

The disclosed transducer apparatuses are shaped such that adjacent transducer apparatuses in an assembly have complementary convex and concave edges. In an example, a transducer apparatus includes at least one convex edge portion protruding away from a centroid of the array and at least one concave edge portion recessed toward the centroid of the array.

Figure 1A:
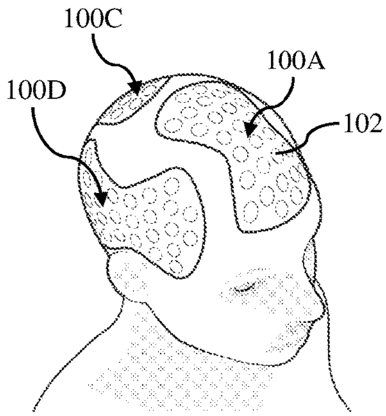
FIGS. 1A-1C depict an example of transducers located on a subject's head.
Figure 1B:
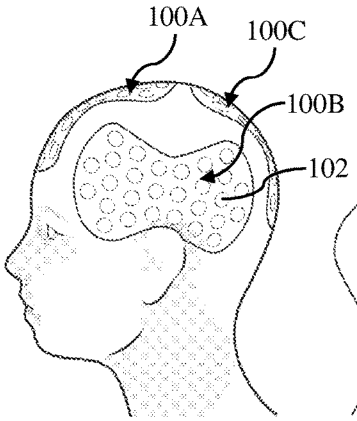
Figure 1C:
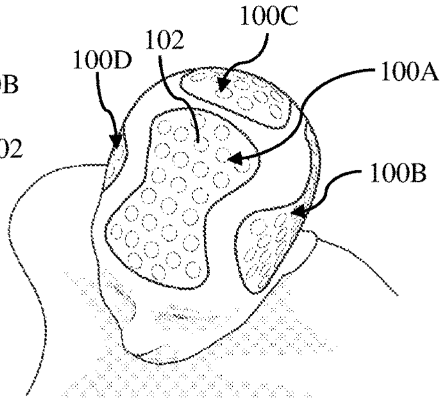

FIGS. 1A-1C depict transducers 100 (e.g., 100A, 100B, 100C, and 100D) positioned on the head of a subject's body. Such an arrangement of transducers 100 is capable of applying TTFields to a tumor in a region of the subject's brain. Various other positions and/or orientations on the subject's head may be selected for placement of transducers. Each transducer 100 may have an array of electrode elements 102 disposed thereon. Each transducer 100 may be placed on a subject's head with a face of the array of electrode elements 102 facing and conforming to the subject's head. As illustrated, the transducers 100 on the subject's head are arranged in an interlocking pattern with interconnecting concave/convex edge portions of adjacent transducers 100.

Figure 2A:
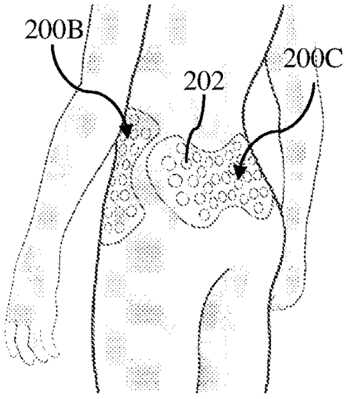
FIGS. 2A-2C depict an example of transducers located on a subject's torso.
Figure 2B:
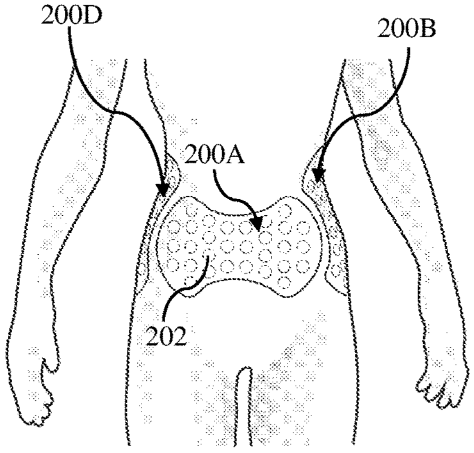
Figure 2C:
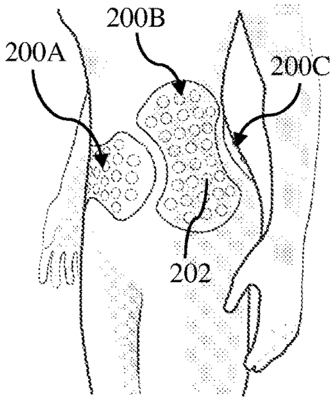

FIGS. 2A-2C depict transducers 200 (e.g., 200A, 200B, 200C, 200D) attached to other portions (e.g., a torso/abdomen) of the subject's body. Various other positions and/or orientations on the subject's torso may be selected for placement of transducers. Each of the transducers 200 may have an array of electrode elements 202 disposed thereon. Each transducer 200 may be placed over the subject's body with a face of the array of electrode elements 202 facing and conforming to the subject's body. As illustrated, the transducers 200 on the subject's torso are arranged substantially in a line wrapping around the torso of the subject's body with interconnecting concave/convex edge portions of adjacent transducers 200. In an example, the transducers 100, 200 of FIGS. 1A-1C and 2A-2C may be affixed to the subject's body via a medically appropriate gel or adhesive. In another example, the transducers 100, 200 may be attached to one or more garments and held against the subject's body.

Figure 3A:
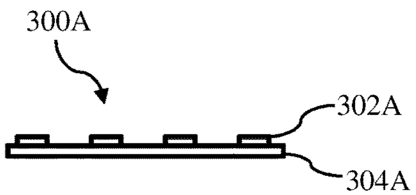
FIGS. 3A and 3B are cross-sectional views of example structures of transducers.
Figure 3B:
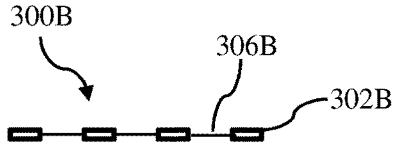

The structure of the transducers may take many forms. In FIG. 3A, a transducer 300A has a plurality of electrode elements 302A positioned on a substrate 304A. The substrate 304A is configured for attaching the transducer 300A to a subject's body. Suitable materials for the substrate 304A include, for example, cloth, foam, flexible plastic, and/or a conductive medical gel. The transducer 300A may be affixed to the subject's body via the substrate 304A (e.g., via an adhesive layer and/or the conductive medical gel). The transducer may be conductive or non-conductive. FIG. 3B depicts another example of the structure of a transducer 300B. In this example, the transducer 300B includes a plurality of electrode elements 302B that are electrically and mechanically connected to one another without a substrate. In one example, electrode elements 302B are connected to each other through conductive wires 306B.

The transducers 300A and 300B may comprise arrays of substantially flat electrode elements 302A and 302B, respectively. The array of electrode elements may be capacitively coupled. In an example, the electrode elements 302A and 302B are ceramic elements having a ceramic dielectric layer. In another example, the electrode elements 302A and 302B are non-ceramic dielectric materials positioned over a plurality of flat conductors such as, for example, polymer films disposed over pads on a printed circuit board or over flat pieces of metal.

Conventionally, the dielectric material (e.g. ceramic disks or polymer films) faces toward the skin-contact side of the transducer array and contact with the skin is made via a conductive medical gel or conductive adhesive on the dielectric material. Each electrode has a conductive (metal) element on the other side of the dielectric material and the electrodes are coupled via conductive wires or a PCB trace, and via a connector to the AC power supply. The PCB or wiring is usually sandwiched in a layer between the electrode elements and the substrate 304A (e.g. adhesive bandage or plaster) which may provide an adhesive layer around the perimeter of the electrode array and, optionally, in gaps between rows or columns of electrode elements. The adhesive adheres to the subject's skin to help keep the transducer array in place on the subject's body. In some embodiments, strips of foam or flexible material with cut-outs for the electrodes are used to keep the electrodes in position and add a more comfortable contour around the edge of the electrodes (e.g. ceramic disks). In an embodiment, the foam strips can extend to fill the gaps between rows/columns of the electrodes (or can be used as a complete layer with cut-outs for the electrodes) thereby intercepting the PCB trace or wiring from contacting the skin for added comfort. The latter construct, however, produces a large central area of the transducer that is not adhered to the skin, and the transducer is not well secured, and, moreover, the medical gel may not be able to maintain contact for the electrodes on the skin (resulting in a much reduced electric field intensity entering the body).

In some embodiments, a sheet of conductive anisotropic material, for example graphite, may be located between the dielectric material and the skin. In some embodiments, the sheet of anisotropic material may be a sheet of pyrolytic graphite. In some embodiments, the anisotropic material may be graphite foil made from compressed high purity exfoliated mineral graphite, or graphitized polymer film. In some embodiments, the anisotropic material may be non-metallic.

The sheet of conductive anisotropic material may be a sheet of graphite. An example of pyrolytic graphite is Pyrolytic Graphite Sheet (PGS), available from Panasonic Industry, Kadoma, Osaka, Japan. An example of graphite foil made from compressed high purity exfoliated mineral graphite is MinGraph® 2010A Flexible Graphite, available from Mineral Seal Corp., Tucson, Arizona, USA. An example of graphitized polymer film, e.g., graphitized polyimide film, is supplied by Kaneka Corp., Moka, Tochigi, Japan. In alternative embodiments, conductive anisotropic materials other than graphite may be used instead of graphite.

The area of the sheet of anisotropic material may cover all electrode elements and include additional area corresponding to a concave or convex fit, according to embodiments disclosed herein. When viewed in a direction perpendicular to the surface of the sheet, the area of the sheet of anisotropic material may define the area of the electrode array. The sheet of anisotropic material may be electrically connected to the electrode array (or, optionally, to the dielectric layer) via a layer of hydrogel or conductive adhesive and may be connected to the skin via a layer of hydrogel or conductive adhesive.

The sheet of anisotropic material may have a (skin-facing) front face and a rear face. A skin contact layer comprising a conductive adhesive composite may be disposed on the front face of the anisotropic material sheet. The dielectric layer may be positioned on the rear face side of the anisotropic material sheet, and the dielectric layer may have a front face disposed in electrical contact with the rear face of the sheet. In some embodiments, the anisotropic material sheet may have a first resistance in a direction that is perpendicular to the front face, and the resistance of the anisotropic material sheet in directions that are parallel to the front face may be, for example, less than half of the first resistance. Accordingly, current may be spread across the whole area of the anisotropic material sheet and pass to the skin across the whole area of the anisotropic material sheet (see, for example, U.S. patent application Ser. No. 17/880,937, filed Aug. 4, 2022, and Ser. No. 17/899,220, file Aug. 30, 2022).

As contemplated herein, a more secure attachment of the transducer array to the body can be achieved. A first adhesive substrate may be used in a layer between the electrode elements and the PCB trace or wiring, optionally with a cut-out for the electrode elements, in order to provide better adhesion to the skin, including in the central area of the array, while protecting the skin from any sharp edges from the PCB trace or wiring. In a first embodiment, this first adhesive substrate may be an adhesive bandage or plaster, optionally with cut-outs for the electrodes. Alternatively, in a second embodiment, the foam layer (or foam strips between rows/columns of electrodes), optionally with a cut-out for the electrode elements, may have an adhesive layer on the skin-facing side of the foam to improve attachment to the body. In both cases, optionally, a second substrate layer (e.g. adhesive bandage or plaster) may cover the exterior-facing side of the transducer array, to hold the PCB trace/wiring in place, and, further optionally, may provide a surrounding adhesive layer or strip on the second substrate layer around the perimeter of the array to hold the whole construct in place. This layered construct, with the PCB trace/wiring located on the exterior-facing side of a (first) substrate layer, provides good adhesion to the body over most of the transducer array, while protecting the skin from irritation due to any sharp edges of the PCB trace/wiring.

The shapes of electrode elements that contact the body (e.g. ceramic or polymeric dielectric layer) may take any shape. For example, FIG. 4B shows electrode elements that are rectangular or elongated strips with rounded ends, where the strips may differ in length according to a preferred packing to fill the transducer shape, and FIGS. 4C and 4D show hexagonal electrode elements, which may also have rounded vertices. For simplicity, FIG. 4A and FIGS. 5A-5D show circular electrode shapes (disk shape), although in other embodiments other electrode shapes could also be used, including combinations of different shape electrode elements on a single transducer array. For example, each of the electrode elements in the array, individually, may have a shape selected from: circular or disk-shaped or substantially disk-shaped; oval, ovaloid, ovoid, or elliptical; square, rectangular or hexagonal shape; substantially square, rectangular or hexagonal shape with one or more rounded corners; triangular shape; substantially triangular shape with rounded corners or one or more rounded edge; truncated triangular shape; substantially truncated triangular shape with rounded corners or one or more rounded edge; wedge shape; substantially wedge shape with rounded corners; truncated wedge shape; or substantially truncated wedge shape with rounded corners or one or more rounded edge.

Various shapes of transducers may be used to maximize a number of electrode elements that can be located at an area of the subject's body. For example, as disclosed herein, the transducer may be shaped to fit together with one or more adjacent transducers located on the subject's body.

FIGS. 4A-4D and 5A-5D depict assemblies of transducers for applying tumor treating fields to a subject's body. Assemblies depicted in FIGS. 4A-4D may be used for the placement of transducers on a subject's head (e.g., FIGS. 1A-1C), or for the placement of transducers on any other parts (e.g., torso) of a subject's body. Assemblies depicted in FIGS. 5A-5D are arranged in a line, and such arrangements may be used for placement of transducers around a torso of a subject's body (e.g., FIGS. 2A-2C), or on any other part of the subject's body. Each assembly in FIGS. 4A-4D and 5A-5D depicts four transducers shaped to fit together, but other numbers (e.g., two or three) of transducers may be shaped to fit together in other embodiments.

In each of FIGS. 4A-5D, the illustrated assembly includes a first transducer array (400A, 430A, 450A, 470A, 500A, 530A, 550A, 570A) ("first array") having a first surface for placement over the subject's body. The first array in each of FIGS. 4A-5D includes a plurality of electrode elements (402, 432, 452, 472, 502, 532, 552, 572). The assembly further includes a second transducer array (400B, 430B, 450B, 470B, 500B, 530B, 550B, 570B) ("second array") similarly including a plurality of electrode elements and having a second surface for placement over the subject's body. As illustrated, the first surface of the first array (400A, 430A, 450A, 470A, 500A, 530A, 550A, 570A) and the second surface of the second array (400B, 430B, 450B, 470B, 500B, 530B, 550B, 570B) have complementary shapes capable of fitting together adjacent to each other on a surface of the subject's body without overlapping each other.

In each of FIGS. 4A-5D, the assembly further includes a third transducer array (400C, 430C, 450C, 470C, 500C, 530C, 550C, 570C) ("third array") and a fourth transducer array (400D, 430D, 450D, 470D, 500D, 530D, 550D, 570D) ("fourth array"). The first array (400A, 430A, 450A, 470A, 500A, 530A, 550A, 570A) and the third array (400C, 430C, 450C, 470C, 500C, 530C, 550C, 570C) may form a first pair of transducer arrays capable of generating a TTField therebetween. The second array (400B, 430B, 450B, 470B, 500B, 530B, 550B, 570B) and the fourth array (400D, 430D, 450D, 470D, 500D, 530D, 550D, 570D) may form a second pair of transducer arrays capable of generating a second TTField therebetween. Like the first and second arrays, the third array and the fourth array each include a plurality of electrode elements and have a third surface and a fourth surface, respectively, for placement over the subject's body. The first surface of the first array, the second surface of the second array, the third surface of third array, and the fourth surface of the fourth array may each have shapes capable of fitting together with complementary shaped concave or convex edge portions of at least two other arrays in the group of four transducer arrays without overlapping each other.

Figure 4A:
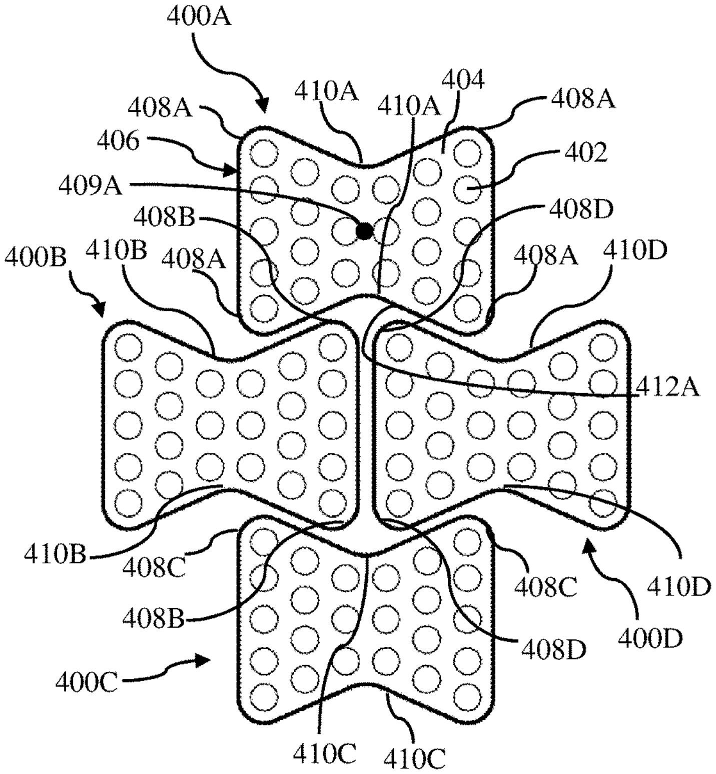
FIGS. 4A-4D depict example layouts of complementary shaped transducer arrays.
Figure 4B:
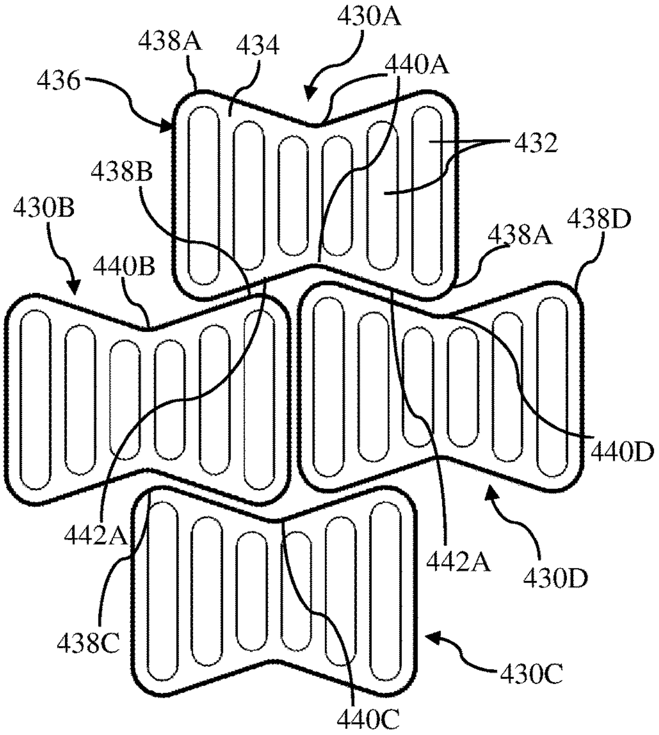
Figure 4C:
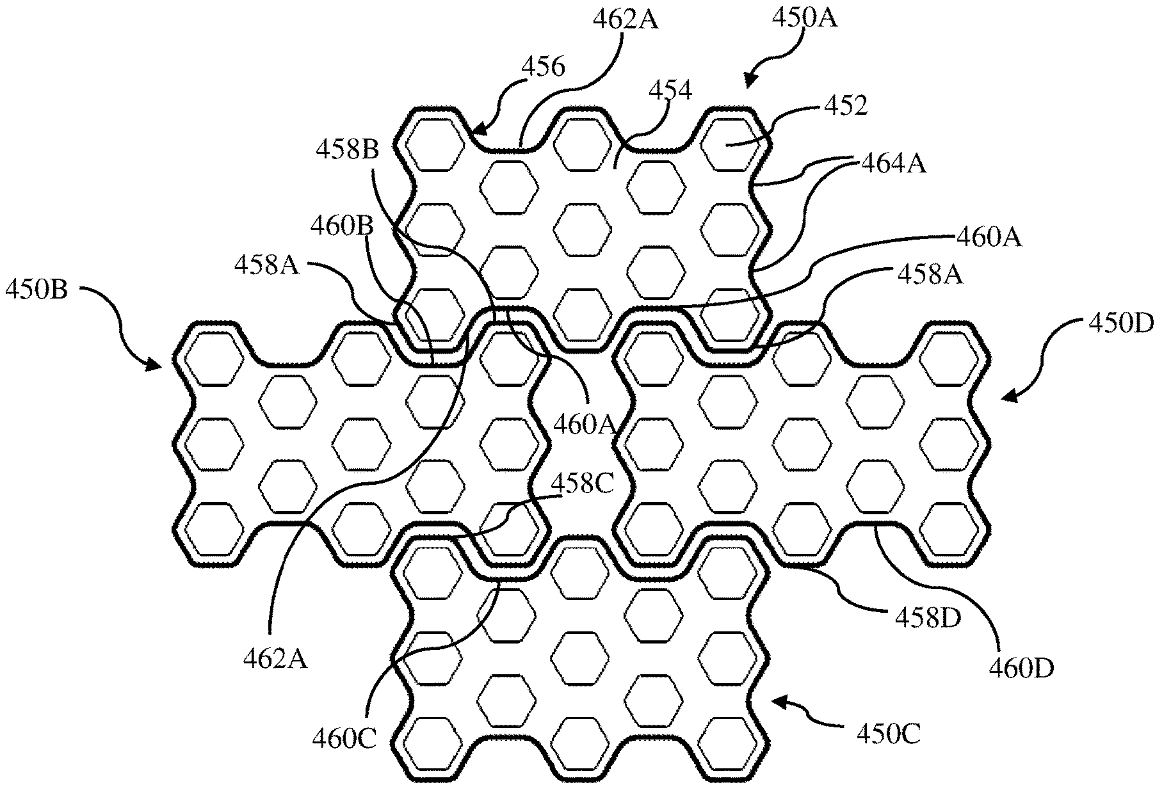
Figure 4D:
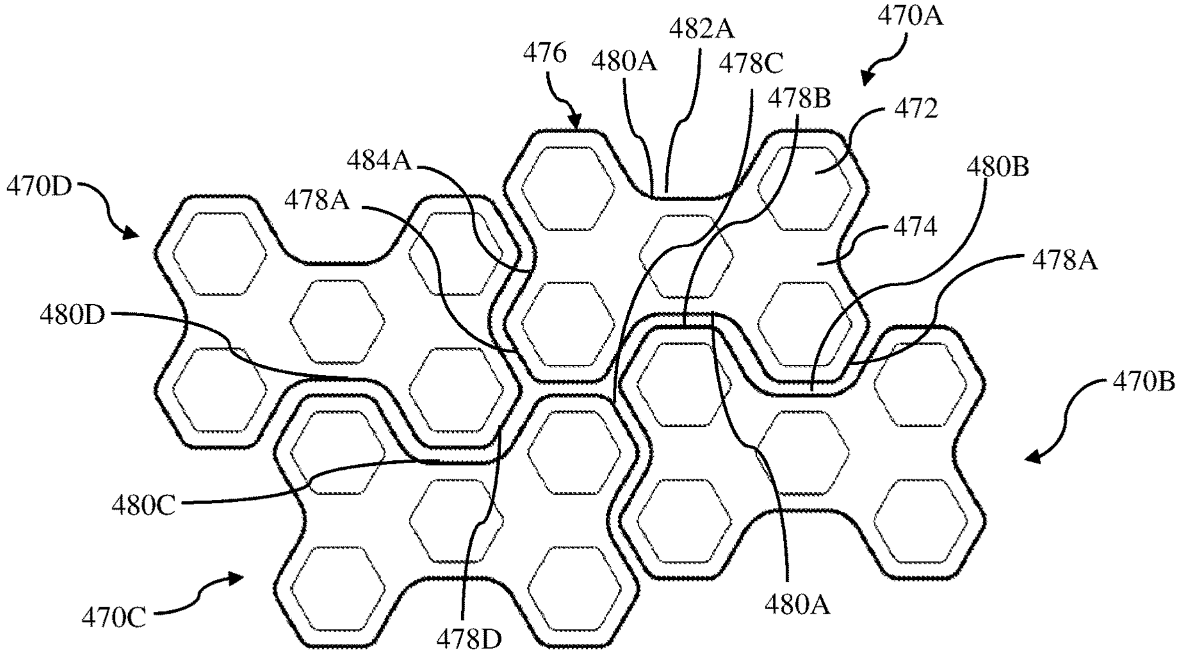
Figure 5A:
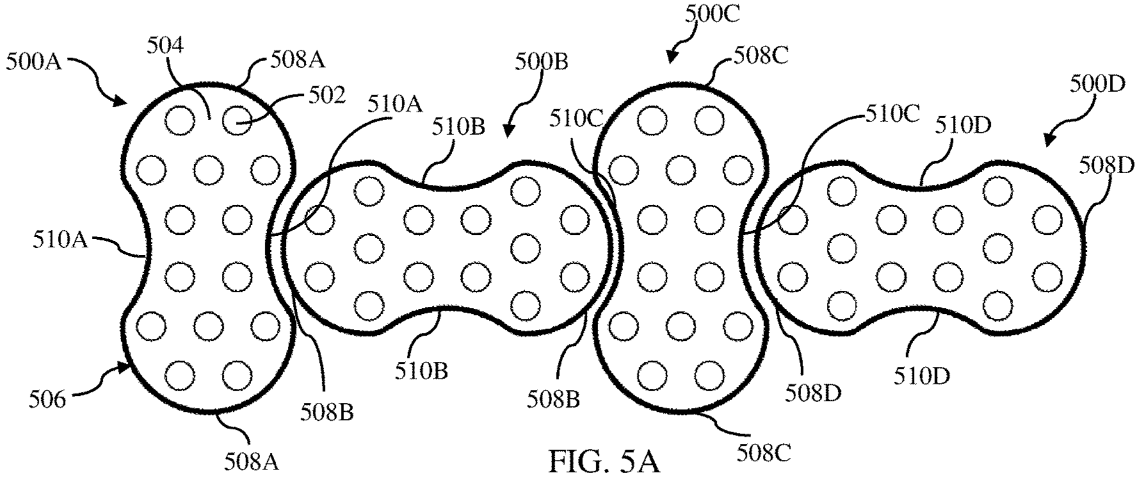
FIGS. 5A-5D depict other example layouts of complementary shaped transducer arrays.
Figure 5B:
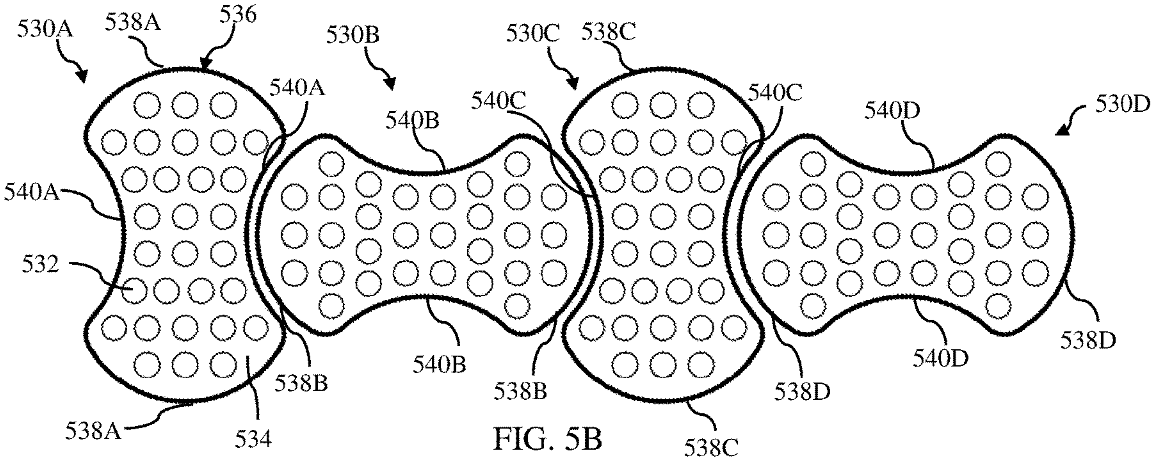
Figure 5C:
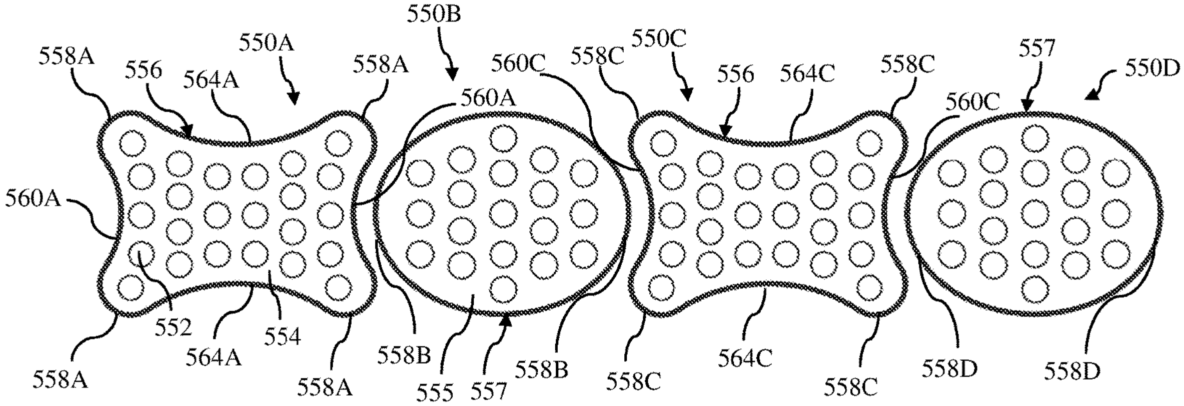
Figure 5D:
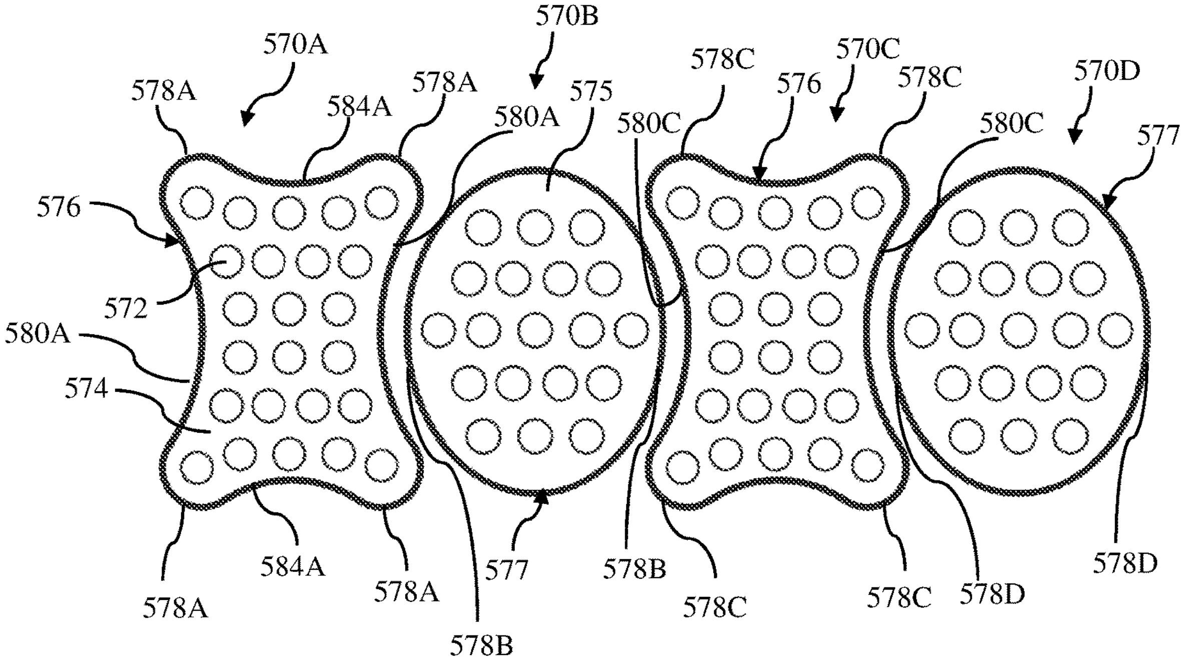

In FIGS. 4A-5D, the first surface of the first array is indicated by reference numeral 404, 434, 454, 474, 504, 534, 554, and 574. In an example, the "surface" (e.g., first surface 404, 434, 454, 474, 504, 534, 554, 574) of each transducer array (e.g., first array 400A, 430A, 450A, 470A, 500A, 530A, 550A, 570A) may be a continuous surface in the form of a substrate (e.g., substrate 304A of FIG. 3A). In another example, the "surface" of each transducer array may include one or more components (e.g., electrode elements, a PCB, and/or conductive wires (i.e., 306B of FIG. 3B)), that together define an outer perimeter of the transducer array. In FIGS. 4A-4D, 5A, and 5B, the first surface (404, 434, 454, 474, 504, 534) of the first array (400A, 430A, 450A, 470A, 500A, 530A) may have substantially the same shape as a corresponding second surface of the second array (400B, 430B, 450B, 470B, 500B, 530B). In FIGS. 5C and 5D, the surface (554, 574) of the first array (550A, 570A) has a different shape than a surface (555, 575) of the second array (550B, 570B), and the first surface (554, 574) has an outer perimeter (556, 576) that is different than an outer perimeter (557, 577) of the second surface (555, 575).

In FIG. 4A, the arrays 400A-D have similar or the same surfaces 404 and outer perimeter 406 as the surfaces 434 and outer perimeter 436 of the arrays 430A-D in FIG. 4B. In FIGS. 4A and 4B, one difference between the two assemblies of transducer arrays 400A-D and 430A-D is the shape and/or type of electrode elements 402 and 432, respectively. FIG. 4A shows electrode elements 402 that are circular or disk shaped, while FIG. 4B shows electrode elements 432 that are elongated and arranged parallel with respect to each other. Any desired shape and/or type of electrode elements may be used with any of the transducer arrays described herein, and variations thereof. FIGS. 4A and 4B also show that the geometric fit need not be the "best" geometric fit (for example, optimizing symmetry in FIG. 4A, compared to slightly askew in FIG. 4B).

In FIGS. 4A-5D, the outer perimeter (406, 436, 456, 476, 506, 536, 556, 576) of the first surface (404, 434, 454, 474, 504, 534, 554, 574) has one or more concave edge portions (410A, 440A, 460A, 480A, 510A, 540A, 560A, 580A). As shown in FIG. 4A, when viewed from a direction perpendicular to the face of the first array 400A, the first outer perimeter 406 substantially tracing the electrode elements 402 may have a shape including at least one convex edge portion 408A protruding away from a centroid 409A of the array, and at least one concave edge portion 410A recessed toward the centroid 409A. In FIG. 4A, the at least one concave edge portion 410A is capable of tracing, abutting, or enclosing at least a portion of a convex edge (e.g., 408B, 408D) having a substantially similar or same shape line segment as the at least one concave edge portion 410A. FIGS. 4B-5D each similarly show a first array (430A, 450A, 470A, 500A, 530A, 550A, 570A) including at least one convex edge portion (438A, 458A, 478A, 508A, 538A, 558A, 578A) and at least one concave edge portion (440A, 460A, 480A, 510A, 540A, 560A, 580A).

In FIGS. 4A, 4B, 5A, and 5B, the outer perimeter (406, 436, 506, 536) of the first array (400A, 430A, 500A, 530A) has a shape including two concave edge portions (410A, 440A, 510A, 540A) and at least two convex edge portions (408A, 438A, 508A, 538A). In FIGS. 4D, 5C, and 5D, the outer perimeter (476, 556, 576) of the first array (470A, 550A, 570A) has a shape including four concave edge portions (480A/484A, 560A/564A, 580A/584A). In FIG. 4C, the outer perimeter (456) of the first array (450A) has a shape including eight concave edge portions (460A/464A). Other numbers of concave edge portions may be possible in other embodiments. In FIGS. 4C, 4D, 5C, and 5D, the outer perimeter (456, 476, 556, 576) of the first array includes at least one pair of concave edge portions (460A, 480A, 560A, 580A) located on opposite sides of the array from each other, and at least another pair of concave edge portions (464A, 484A, 564A, 584A) located on opposite sides of the array from each other, where the one pair of concave edge portions have different shape line segments than the other pair of concave edge portions.

As shown in FIGS. 4A-4D, the concave edge portion (410A, 440A, 460A, 480A) may be partially defined by a straight line (412A, 442A, 462A, 482A). Similarly, a corresponding convex edge portion (408B, 438A, 458B, 478A) may be at least partially defined by a straight line. In addition, the concave edge portion (410A, 440A, 460A, 480A) may be at least partially defined by a second straight line. In FIGS. 5A-5D, the concave edge portion (510A, 540A, 560A, 580A) is at least partially defined by a curve. Similarly, a corresponding convex edge portion (508B, 538B, 558B, 578B) may be at least partially defined by a curve. As shown in FIGS. 5A-5D, the curves of the concave edge portion (510A, 540A, 560A, 580A) and corresponding convex edge portion (508B, 538B, 558B, 578B) may have the same, or approximately the same, radius of curvature. However, the curve of the concave edge portion need not have the same radius of curvature as the curve of the corresponding convex edge portion. For example, in FIG. 5C, rotation of arrays 550A and 550C by 90 degrees would also result in geometrically fitting arrays of the invention, and this configuration would present concave edge portions (564A, 564C) adjacent to convex edge portions (558B, 558D) where concave edge portions (564A, 564C) would have a larger radius of curvature than the curve of the corresponding convex edge portions (558B, 558D).

In FIGS. 4A-5D, the outer perimeter of the surface of the second array (400B, 430B, 450B, 470B, 500B, 530B, 550B, 570B) has one or more convex edge portions (408B, 438B, 458B, 478B, 508B, 538B, 558B, 578B) sized and shaped to fit into, against, or immediately adjacent the at least one concave edge portion (410A, 440A, 460A, 480A, 510A, 540A, 560A, 580A) of the outer perimeter (406, 436, 456, 476, 506, 536, 556, 576) of the first array. For example, in FIGS. 4A and 4B, one convex edge portion (408B, 438B) of the second array (400B, 430B) is in a space adjacent the concave edge portion (410A, 440A) at the lower edge of the first array (400A, 430A). The concave edge portion (410A, 440A, 460A, 480A, 510A, 540A, 560A, 580A) and convex edge portion (408B, 438B, 458B, 478B, 508B, 538B, 558B, 578B) may fit together such that they are equidistant from each other along a portion of their lengths.

As in FIGS. 4A-5B, the outer perimeter of the surface of the second array (400B, 430B, 450B, 470B, 500B, 530B) may also include one or more concave edge portions (410B, 440B, 460B, 480B, 510B, 540B). As in FIGS. 5C and 5D, the outer perimeter (557, 577) of the surface of the second array (550B, 570B) may be entirely convex in shape. As in FIGS. 4A-5B, the outer perimeter of the surface of the second array (400B, 430B, 450B, 470B, 500B, 530B) may be equivalent to the first outer perimeter (406, 436, 456, 476, 506, 536).

In FIGS. 4A-4D, the one or more convex edge portions (408A, 438A, 458A, 478A) of the first array (400A, 430A, 450A, 470A) may be sized to fit into, against, or immediately adjacent concave edge portion(s) (410B, 440B or 440D, 460B, 480B) of the second array (400B, 430B or 430D, 450B, 470B) at the same time that one or more convex edge portions (408B, 438B or 438D, 458B, 478B) of the second array (400B, 430B or 430D, 450B, 470B) are fitted into, against, or immediately adjacent concave edge portion(s) (410A, 440A, 460A, 480A) of the first array (400A, 430A, 450A, 470A).

In FIGS. 4A-5D, the outer perimeter of the surface of the third array (400C, 430C, 450C, 470C, 500C, 530C, 550C, 570C) includes one or more concave edge portions (410C, 440C, 460C, 480C, 510C, 540C, 560C, 580C) and one or more convex edge portions (408C, 438C, 458C, 478C, 508C, 538C, 558C, 578C). In addition, the outer perimeter of the surface of the fourth array (400D, 430D, 450D, 470D, 500D, 530D, 550D, 570D) may include one or more convex edge portions (408D, 438D, 458D, 478D, 508D, 538D, 558D, 578D). In FIGS. 4A-5B, the outer perimeter of the surface of the fourth array (400D, 430D, 450D, 470D, 500D, 530D) may also include one or more concave edge portions (410D, 440D, 460D, 480D, 510D, 540D). In other embodiments, e.g., as shown in FIGS. 5C and 5D, the outer perimeter of the surface of the fourth array (550D, 570D) may be entirely convex in shape. As shown in FIGS. 4A-5D, the outer perimeter of the surface of the third array (400C, 430C, 450C, 470C, 500C, 530C, 550C, 570C) may be equivalent to the outer perimeter (406, 436, 456, 476, 506, 536, 556, 576) of the first array (400A, 430A, 450A, 470A, 500A, 530A, 550A, 570A), while the outer perimeter of the surface of the fourth array (400D, 430D, 450D, 470D, 500D, 530D, 550D, 570D) may be equivalent to the outer perimeter of the surface of the second array (400B, 430B, 450B, 470B, 500B, 530B, 550B, 570B).

The "outer perimeter" of a transducer array may correspond to any of the following arrangements relative to a substrate (e.g., 304A of FIG. 3A) of a transducer. The outer perimeter (406, 436, 456, 476, 506, 536, 556, 576) of the array may substantially correspond to an outer perimeter of the substrate upon which the electrode elements (for example, electrode elements of the first array, 402, 432, 452, 472, 502, 532, 552, 572) are disposed. In an example, the outer perimeter (for example, perimeter of the first array, 406, 436, 456, 476, 506, 536, 556, 576) conforms entirely to the outer perimeter of the substrate. In another example, the outer perimeter (for example, perimeter of the first array, 406, 436, 456, 476, 506, 536, 556, 576) substantially conforms to the outer perimeter of the substrate excluding areas where slits are formed along an outer shape of the substrate.

The outer perimeter (406, 436, 456, 476, 506, 536, 556, 576) of the array may take many possible shapes. For example, when viewed in a direction perpendicular to the face of the array, the outer perimeter (for example, perimeter of the first array, 406, 436, 456, 476, 506, 536, 556, 576) may have a substantially bow-tie shape (e.g., FIGS. 4A/4B), a substantially infinity symbol shape (e.g., FIG. 5B), a substantially peanut shell shape (e.g., FIG. 5A), or a substantially butterfly shape (e.g., FIG. 4D/5C/5D). The outer perimeter may take other possible shapes and variations of the shapes illustrated herein without departing from the scope of the present disclosure.

The transducer arrays may fit together in different ways. As in FIGS. 5A-5D, a single concave edge portion (510A, 540A, 560A, 580A) of the first array (500A, 530A, 550A, 570A) may be sized/shaped to fit around, against, or immediately adjacent to only one convex edge portion (508B, 538B, 558B, 578B) of the second array (500B, 530B, 550B, 570B) or one convex edge portion (508D, 538D, 558D, 578D) of the fourth array (500D, 530D, 550D, 570D) at a time. Alternatively, a single concave edge portion of an array may be sized/shaped to fit around, against, or immediately adjacent to two convex edge portions of two different adjacent arrays at the same time. For example, as shown in FIG. 4A, a single concave edge portion (410A) of the first array (400A) may be sized/shaped to fit around, against, or immediately adjacent to both a convex edge portion (408B) of the second array (400B) and a convex edge portion (408D) of the fourth array (400D) at the same time. Further, a concave edge portion (410C) of the third array (400C) may fit around, against, or immediately adjacent to a convex edge portion (408B) of the second array (400B) and a convex edge portion (408D) of the fourth array (400D).

Figure 6:
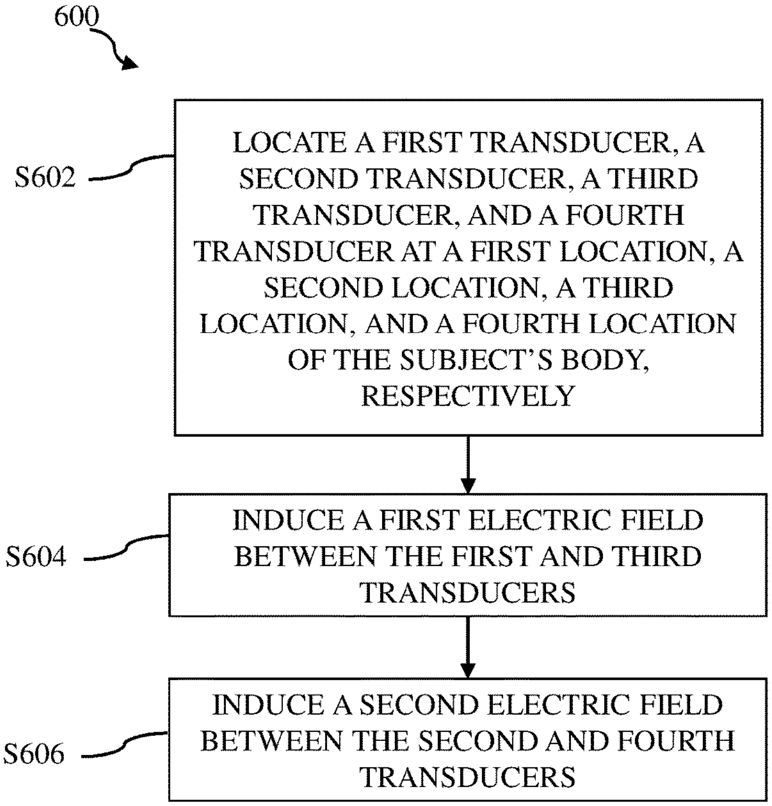
FIG. 6 is a flowchart depicting an example of applying TTFields to a subject's body.

FIG. 6 depicts an example method 600 of applying TTFields to a subject's body in accordance with the present techniques. The method 600 begins at step S602 with locating a first transducer, a second transducer, a third transducer, and a fourth transducer at a first location, a second location, a third location, and a fourth location of the subject's body, respectively. The first transducer may have a concave edge portion and the second transducer may have a convex edge portion. The convex edge portion of the second transducer located at the second location may be positioned into a space defined by the concave edge portion of the first transducer located at the first location without overlapping the concave edge portion. At step S604, the method 600 includes inducing a first electric field between the first transducer and the third transducer. At step S606, the method 600 includes inducing a second electric field between the second transducer and the fourth transducer. As illustrated in FIGS. 1A-C, 2A-C, and 4A-5D, edge portions of each of the first, second, third, and fourth transducers located at the first, second, third, and fourth locations, respectively, may interface with complementary shaped edge portions of two other transducers in the group of the first, second, third, and fourth transducers.

The fourth transducer may have a convex edge portion that is positioned into a space defined by another concave edge portion of the first transducer. As in FIGS. 2A-2C, this other concave edge portion of the first transducer may be opposite to the concave edge portion at which the second transducer is positioned. Any of the transducer layouts described with reference to FIGS. 5A-5D above may be positioned in this manner (i.e., in a line capable of connecting one end to the other end if, for example, connected in an oval/circle around a torso of the subject's body). For the arrays positioned in this manner, and as shown in FIGS. 2A-2C, step S604 of the method 600 includes inducing a first electric field between the first transducer (200A) and the third transducer (200C) and step S606 of the method 600 includes inducing a second electric field between the second transducer (200B) and the fourth transducer (200D), such that the first electric field and the second electric field are induced through the subject's body, the first electric field being perpendicular (or approximately perpendicular) to the second electric field. In FIGS. 4A-4D, the arrays may be applied grouped on a relatively flat body surface (approaching 2-dimensional), or may be applied grouped on a curved body surface like the head (3-dimensional). In the first scenario (approaching 2-dimensional), the first and third locations corresponding to the locations of the first and third transducers may be located in a first line with respect to a surface of the subject's body, and the second and fourth locations corresponding to the locations of the second and fourth transducers may be located in a second line with respect to the surface of the subject's body. For example, in FIGS. 4A-C, the first line and the second line may be perpendicular to each other (e.g., the first and third transducers are in vertical alignment while the second and fourth transducers are in horizontal alignment). In this first scenario, the electric fields applied as discussed above may be used to treat near-surface tumors, or the set up could be used for near-surface impedance measurements. In the second scenario (3-dimensional), the arrays of FIG. 4A and FIG. 4B, for example, could be applied to a subject's head in the manner shown in FIGS. 1A-1C (for example, the second array 400B and the fourth array 400D could be placed anterior and posterior, and the first array 400A and the third array 400C could be placed on the left and right side of the head such that the upper concave edge 410A and the lower concave edge 410C of FIG. 4A contour above the subject's ears). In this second scenario, the electric fields applied as discussed above may be used to treat a target area of the brain (e.g., a tumor in the brain or resection cavity area in the brain) such that the first electric field is perpendicular (or approximately perpendicular) to the second electric field.

The method 600 of FIG. 6 may be performed with any of the transducer array layouts described at length above with reference to FIGS. 4A-5D, or any variation thereof. The first, second, third, and fourth locations may be on a head of the subject's body (e.g., FIGS. 1A-1C), or may be on a torso of the subject's body (e.g., FIGS. 2A-2C). For each assembly of complementary transducer arrays, each transducer array may have the same shape, or differing shapes.

The invention includes other illustrative embodiments ("Embodiments") as follows.

Embodiment 1: A transducer apparatus for delivering tumor treating fields to a subject's body, the transducer apparatus comprising: an array of electrode elements, the array configured to be positioned over the subject's body with a face of the array facing the subject's body; wherein, when viewed from a direction perpendicular to the face of the array, an outer perimeter of the array substantially tracing the electrode elements has a shape comprising: at least one convex edge portion protruding away from a centroid of the array; and at least one concave edge portion recessed toward the centroid of the array.

Embodiment 2: The transducer apparatus of Embodiment 1, wherein the at least one concave edge portion is capable of tracing, abutting, or enclosing at least a portion of a convex edge having a substantially similar or same shape line segment as the concave edge portion.

Embodiment 3: The transducer apparatus of Embodiment 1, wherein the at least one concave edge portion is partially defined by a straight line.

Embodiment 4: The transducer apparatus of Embodiment 3, wherein the at least one concave edge portion is at least partially defined by a second straight line.

Embodiment 5: The transducer apparatus of Embodiment 1, wherein the at least one convex edge portion is partially defined by a straight line.

Embodiment 6: The transducer apparatus of Embodiment 1, wherein the at least one concave edge portion is at least partially defined by a curve.

Embodiment 7: The transducer apparatus of Embodiment 6, wherein the at least one convex edge portion is at least partially defined by a second curve, wherein the curve and the second curve have the same radius of curvature.

Embodiment 8: The transducer apparatus of Embodiment 6, wherein the at least one convex edge portion is at least partially defined by a second curve, wherein the curve has a larger radius of curvature than the second curve.

Embodiment 9: The transducer apparatus of Embodiment 1, wherein the at least one convex edge portion is at least partially defined by a curve.

Embodiment 10: The transducer apparatus of Embodiment 1, further comprising a substrate, wherein the array of electrode elements is disposed on the substrate, and the outer perimeter of the array substantially corresponds to an outer perimeter of the substrate.

Embodiment 11: The transducer apparatus of Embodiment 10, wherein the outer perimeter of the array conforms entirely to the outer perimeter of the substrate.

Embodiment 12: The transducer apparatus of Embodiment 10, wherein the outer perimeter of the array substantially conforms to the outer perimeter of the substrate excluding areas where slits are formed along an outer shape of the substrate.

Embodiment 13: The transducer apparatus of Embodiment 1, further comprising a substrate, wherein the array of electrode elements is disposed on the substrate, wherein the outer perimeter of the array has substantially the same shape as an outer perimeter of the substrate, and wherein the outer perimeter of the array is smaller than the outer perimeter of the substrate.

Embodiment 14: The transducer apparatus of Embodiment 1, wherein, when viewed from the direction perpendicular to the face of the array, the outer perimeter of the array has a substantially bow-tie, infinity symbol, peanut shell, or butterfly shape.

Embodiment 15: The transducer apparatus of Embodiment 1, wherein, when viewed from the direction perpendicular to the face of the array, the outer perimeter of the array has a shape comprising: at least m concave edge portions; and at least n convex edge portions; wherein m=2 or m=4, and wherein n=2 or n=4.

Embodiment 16: The transducer apparatus of Embodiment 15, wherein m=4 and the at least four concave edge portions comprise: a first pair of concave edge portions on opposite sides of the array from each other; and a second pair of concave edge portions on opposite sides of the array from each other; the first pair of concave edge portions have different shape line segments than the second pair of concave edge portions Embodiment 17: The transducer apparatus of Embodiment 1, wherein the electrode elements comprise a ceramic dielectric layer.

Embodiment 18: The transducer apparatus of Embodiment 1, wherein the electrode elements comprise polymer films.

Embodiment 19: The transducer apparatus of Embodiment 1, wherein, when viewed from the direction perpendicular to the array face, the outer perimeter of the array substantially tracing the electrode elements has a shape comprising: at least eight concave edge portions.

Embodiment 20: An assembly for applying tumor treating fields to a subject's body, the assembly comprising: a first transducer array comprising one or more electrode elements, the first transducer array having a first surface for placement over the subject's body; wherein, when viewed in a direction perpendicular to the first surface, a first outer perimeter of the first surface has one or more concave edge portion; a second transducer array comprising one or more electrode elements, the second transducer array having a second surface for placement over the subject's body; wherein, when viewed in a direction perpendicular to the second surface, a second outer perimeter of the second surface has one or more convex edge portion sized and shaped to fit into, against, or immediately adjacent one or more concave edge portion of the first outer perimeter.

Embodiment 21: The assembly of Embodiment 20, wherein, when viewed in the direction perpendicular to the second surface, the second outer perimeter has an entirely convex shape.

Embodiment 22: The assembly of Embodiment 20, wherein, when viewed in the direction perpendicular to the second surface, the second outer perimeter additionally has one or more concave edge portion.

Embodiment 23: The assembly of Embodiment 20, wherein, when viewed in the direction perpendicular to the second surface, the second outer perimeter is equivalent to the first outer perimeter.

Embodiment 24: The assembly of Embodiment 20, further comprising: a third transducer array comprising one or more electrode elements, the third transducer array having a third surface for placement over the subject's body and a third outer perimeter of the third surface; and a fourth transducer array comprising one or more electrode elements, the fourth transducer array having a fourth surface for placement over the subject's body and a fourth outer perimeter of the fourth surface; wherein the first transducer array and the third transducer array form a first pair of transducer arrays capable of generating a first tumor treating field therebetween; and wherein the second transducer array and the fourth transducer array form a second pair of transducer arrays capable of generating a second tumor treating field therebetween.

Embodiment 25: The assembly of Embodiment 24, wherein the concave edge portion of the first outer perimeter is sized and shaped to fit around, against, or immediately adjacent to only one convex edge portion of the second or fourth outer perimeter at a time.

Embodiment 26: The assembly of Embodiment 24, wherein the one or more concave edge portion of the first outer perimeter is sized and shaped to fit around, against, or immediately adjacent to the convex edge portion of the second outer perimeter and a convex edge portion of the fourth outer perimeter at the same time.

Embodiment 27: The assembly of Embodiment 26, wherein one or more concave edge portion of the third outer perimeter is sized and shaped to fit around, against, or immediately adjacent to another convex edge portion of the second outer perimeter and another convex edge portion of the fourth outer perimeter at the same time that the one or more concave edge portion of the first outer perimeter is fitted around, against, or immediately adjacent to the convex edge portion of the second outer perimeter and the convex edge portion of the fourth outer perimeter.

Embodiment 28: The assembly of Embodiment 24, wherein: when viewed in a direction perpendicular to the third surface, the third outer perimeter of the third surface is equivalent to the first outer perimeter of the first surface; and when viewed in a direction perpendicular to the fourth surface, the fourth outer perimeter of the fourth surface is equivalent to the second outer perimeter of the second surface.

Embodiment 29: The assembly of Embodiment 20, wherein: when viewed in the direction perpendicular to the first surface, the first outer perimeter of the first surface has one or more convex edge portion; when viewed in the direction perpendicular to the second surface, the second outer perimeter of the second surface additionally has one or more concave edge portion; wherein one or more convex edge portion of the first outer perimeter is sized to fit into, against, or immediately adjacent one or more concave edge portion of the second outer perimeter at the same time that one or more convex edge portion of the second outer perimeter is fitted into, against, or immediately adjacent one or more concave edge portion of the first outer perimeter.

Embodiment 30: The assembly of Embodiment 20, wherein, the concave edge portion of the first outer perimeter and the convex edge portion of the second outer perimeter are sized to fit together such that the concave edge portion and convex edge portion are equidistant from each other along their lengths.

Embodiment 31: The assembly of Embodiment 20, wherein the first transducer array further comprises a layer of anisotropic material electrically connected to the one or more electrode elements of the first transducer array and located on a skin-facing side of the electrode elements and wherein, when viewed in the direction perpendicular to the first surface, the first surface corresponds to the area of the layer of anisotropic material of the first transducer array, and wherein the second transducer array further comprises a layer of anisotropic material electrically connected to the one or more electrode elements of the second transducer array and located on a skin-facing side of the electrode elements and wherein, when viewed in the direction perpendicular to the second surface, the second surface corresponds to the area of the layer of anisotropic material of the second transducer array.

Embodiment 32: The apparatus of Embodiment 31, wherein the layer of anisotropic material is a synthetic graphite.

Embodiment 33: The apparatus of Embodiment 31, wherein the layer of anisotropic material is a sheet of pyrolytic graphite, graphite foil made from compressed high purity exfoliated mineral graphite, or graphitized polymer film.

Embodiment 34: The apparatus of Embodiment 31, wherein the layer of anisotropic material is nonmetallic.

Embodiment 35: The apparatus of Embodiment 31, wherein the layer of anisotropic material has a first thermal conductivity in a direction that is perpendicular to a plane of the layer, and wherein thermal conductivity of the layer in directions that are parallel to the plane of the layer is more than two times higher, or more than 10 times higher than the first thermal conductivity.

Embodiment 36: The apparatus of Embodiment 31, wherein the layer of anisotropic material has a first resistance in a direction that is perpendicular to a plane of the layer, and wherein resistance of the layer in directions that are parallel to the plane of the layer is less than half, or less than 10% of the first resistance.

Embodiment 37: An assembly for applying tumor treating fields to a subject's body, the assembly comprising: a first transducer array comprising a plurality of electrode elements, the first transducer array having a first surface for placement over the subject's body; a second transducer array comprising a plurality of electrode elements, the second transducer array having a second surface for placement over the subject's body; wherein at least one of the first transducer array or the second transducer array has at least two concave edge portions; and wherein the first surface of the first transducer array and the second surface of the second transducer array have complementary shapes capable of fitting together adjacent to each other on a surface of the subject's body without overlapping each other.

Embodiment 38: The assembly of Embodiment 37, further comprising: a third transducer array comprising a plurality of electrode elements, the third transducer array having a third surface for placement over the subject's body; a fourth transducer array comprising a plurality of electrode elements, the fourth transducer array having a fourth surface for placement over the subject's body; wherein the first surface of the first transducer array, the second surface of the second transducer array, the third surface of the third transducer array, the fourth surface of the fourth transducer array, have shapes capable of fitting together with complementary shaped concave or convex edge portions of at least two other transducers in the group of the first transducer array, the second transducer array, the third transducer array, and the fourth transducer array on a surface of the subject's body without overlapping each other.

Embodiment 39: A method of applying tumor treating fields to a subject's body, the method comprising: locating a first transducer, a second transducer, a third transducer, and a fourth transducer at a first location, a second location, a third location, and a fourth location of the subject's body, respectively, wherein: the first transducer has a concave edge portion and the second transducer has a convex edge portion; and the convex edge portion of the second transducer located at the second location is positioned into a space defined by the concave edge portion of the first transducer located at the first location without overlapping the concave edge portion; inducing a first electric field between the first transducer and the third transducer; and inducing a second electric field between the second transducer and the fourth transducer.

Embodiment 40: The method of Embodiment 39, wherein each of the first, second, third, and fourth locations are on a head of the subject's body.

Embodiment 41: The method of Embodiment 39, wherein each of the first, second, third, and fourth locations are on a torso of the subject's body.

Embodiment 42: The method of Embodiment 39, wherein convex or concave edge portions of each of the first, second, third, and fourth transducers located at the first, second, third, and fourth locations, respectively, interface with complementary shaped concave or convex edge portions of at least two other transducers in the group of the first, second, third, and fourth transducers.

Embodiment 43: The method of Embodiment 39, wherein: the first transducer has a second concave edge portion opposite the concave edge portion; the fourth transducer has a convex edge portion; and the convex edge portion of the fourth transducer located at the fourth location is positioned into a space defined by the second concave edge portion of the first transducer located at the first location without overlapping the concave edge portion.

Embodiment 44: The method of Embodiment 43, wherein: the first and third locations are arranged in a first line with respect to a surface of the subject's body, and the second and fourth locations are arranged in a second line with respect to the subject's body.

Embodiment 45: The method of Embodiment 44, wherein the first line and the second line are perpendicular.

Embodiment 46: The method of Embodiment 39, wherein the first, second, third, and fourth locations are arranged in a line with respect to a surface of the subject's body.

Embodiment 47: An assembly for applying tumor treating fields to a subject's body, the assembly comprising: a first transducer array comprising one or more electrode elements and a layer of anisotropic material electrically connected to the one or more electrode elements, the first transducer array having a first surface for placement over the subject's body; wherein, when viewed in a direction perpendicular to the first surface, a first outer perimeter of the first surface has one or more concave edge portion and is defined by an outer perimeter of the layer of anisotropic material of the first transducer array; a second transducer array comprising one or more electrode elements and a layer of anisotropic material electrically connected to the one or more electrode elements, the second transducer array having a second surface for placement over the subject's body; wherein, when viewed in a direction perpendicular to the second surface, a second outer perimeter of the second surface is defined by an outer perimeter of the layer of anisotropic material of the second transducer array; wherein, when viewed in a direction perpendicular to the second surface, the second outer perimeter of the second surface has one or more convex edge portion sized and shaped to fit into, against, or immediately adjacent one or more concave edge portion of the first outer perimeter.

Embodiment 48: The apparatus of Embodiment 47, wherein the layer of anisotropic material is a synthetic graphite.

Embodiment 49: The apparatus of Embodiment 47, wherein the layer of anisotropic material is a sheet of pyrolytic graphite, graphite foil made from compressed high purity exfoliated mineral graphite, or graphitized polymer film.

Embodiment 50: The apparatus of Embodiment 47, wherein the layer of anisotropic material is nonmetallic.

Embodiment 51: The apparatus of Embodiment 47, wherein the layer of anisotropic material has a first thermal conductivity in a direction that is perpendicular to a plane of the layer, and wherein thermal conductivity of the layer in directions that are parallel to the plane of the layer is more than two times higher, or more than 10 times higher than the first thermal conductivity.

Embodiment 52: The apparatus of Embodiment 47, wherein the layer of anisotropic material has a first resistance in a direction that is perpendicular to a plane of the layer, and wherein resistance of the layer in directions that are parallel to the plane of the layer is less than half, or less than 10% of the first resistance.

Embodiments illustrated under any heading or in any portion of the disclosure may be combined with embodiments illustrated under the same or any other heading or other portion of the disclosure unless otherwise indicated herein or otherwise clearly contradicted by context. For example, and without limitation, embodiments described in dependent claim format for a given embodiment (e.g., the given embodiment described in independent claim format) may be combined with other embodiments (described in independent claim format or dependent claim format).

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A transducer apparatus for delivering tumor treating fields to a subject's body, the transducer apparatus comprising:

an array of electrode elements, the array configured to be positioned over the subject's body with a face of the array facing the subject's body and to deliver tumor treating fields to the subject's body;

wherein, when viewed from a direction perpendicular to the face of the array, an outer perimeter of the array traces the electrode elements and has a shape comprising:

a centroid located within the outer perimeter of the shape;

at least one convex edge portion protruding away from the centroid of the array; and at least one concave edge portion recessed toward the centroid of the array, wherein, when viewed from the direction perpendicular to the face of the array, the at least one convex edge portion and the at least one concave edge portion are complimentary shapes capable of fitting together adjacent to each other on a surface of the subject's body without overlapping each other, wherein, when viewed from the direction perpendicular to the face of the array, the outer perimeter of the array has a bow-tie shape, infinity symbol shape, peanut shell shape, or butterfly shape.

2. The transducer apparatus of claim 1, wherein the at least one concave edge portion is capable of tracing, abutting, or enclosing at least a portion of the convex edge portion.

3. The transducer apparatus of claim 1, wherein the at least one concave edge portion is partially defined by a straight line.

4. The transducer apparatus of claim 1, wherein the at least one convex edge portion is partially defined by a straight line.

5. The transducer apparatus of claim 1, further comprising a substrate, wherein the array of electrode elements is disposed on the substrate, and the outer perimeter of the array corresponds to an outer perimeter of the substrate.

6. The transducer apparatus of claim 1, wherein, when viewed from the direction perpendicular to the face of the array, the outer perimeter of the array has a shape comprising:

at least m concave edge portions; and at least n convex edge portions;

wherein m=2 or m=4, and wherein n=2 or n=4.

7. The transducer apparatus of claim 6, wherein m=4 and the at least four concave edge portions comprise:

a first pair of concave edge portions on opposite sides of the array from each other; and a second pair of concave edge portions on opposite sides of the array from each other;

wherein the first pair of concave edge portions have different shape line segments than the second pair of concave edge portions.

8. The transducer apparatus of claim 1, wherein the at least one convex edge portion and the at least one concave edge portion have line segments of the same or similar shape.

9. The transducer apparatus of claim 1, wherein the outer perimeter of the array has a shape comprising at least two concave edge portions and at least two convex edge portions.

10. The transducer apparatus of claim 9, wherein the shape of the outer perimeter of the array further comprises at most two convex edge portions.

11. The transducer apparatus of claim 1, wherein the outer perimeter of the array has a shape comprising m concave edge portions and n convex edge portions, where m=n.

12. The transducer apparatus of claim 1, wherein the at least one convex edge portion and the at least one concave edge portion are each at least partially defined by a straight line.

13. The transducer apparatus of claim 1, wherein the at least one convex edge portion and the at least one concave edge portion are each at least partially defined by a curve.

14. The transducer apparatus of claim 1, wherein the transducer apparatus is a first transducer apparatus, and, when viewed from the direction perpendicular to the face of the array, the outer perimeter of the array of the first transducer apparatus is capable of fitting together in a complementary and non-overlapping manner with an outer perimeter of an array of a second transducer apparatus having the same shape as the outer perimeter of the first transducer apparatus.

15. The transducer apparatus of claim 1, wherein, when viewed from the direction perpendicular to the face of the array, the outer perimeter of the array excludes any slits.

16. The transducer apparatus of claim 1, wherein the at least one convex edge portion and the at least one concave edge portion provide for adjacent transducer apparatuses to be arranged in an interlocking pattern.

17. A transducer apparatus for delivering tumor treating fields to a subject's body, the transducer apparatus comprising:

an array of electrode elements, the array configured to be positioned over the subject's body with a face of the array facing a subject's body and to deliver tumor treating fields to the subject's body;

wherein, when viewed from a direction perpendicular to the face of the array, an outer perimeter of the array traces the electrode elements and has a shape comprising:

a centroid located within the outer perimeter of the shape;

at least one convex edge portion protruding away from the centroid of the array; and at least one concave edge portion recessed toward the centroid of the array, wherein, when viewed from the direction perpendicular to the face of the array, the outer perimeter of the array has a shape comprising at least two concave edge portions and at least two convex edge portions, wherein, when viewed from the direction perpendicular to the face of the array, the outer perimeter of the array has a bow-tie shape, infinity symbol shape, peanut shell shape, or butterfly shape.

18. The transducer apparatus of claim 17, wherein the shape of the outer perimeter of the array further comprises at most two convex edge portions.

19. The transducer apparatus of claim 17, wherein, when viewed from the direction perpendicular to the face of the array, the at least one convex edge portion and the at least one concave edge portion have line segments of the same or similar shape.

* * * * *